(12) United States Patent
Kang et al.

(10) Patent No.: US 10,406,208 B2
(45) Date of Patent: Sep. 10, 2019

(54) COMPOSITION CONTAINING THYMOSIN BETA 4, AND PHARMACEUTICAL FORMULATION COMPRISING SAME

(71) Applicant: G-TREEBNT CO., LTD., Seongnam-si, Gyeonggi-do (KR)

(72) Inventors: Sin Wook Kang, Seongnam-si (KR); Kyoungsun Kim, Busan (KR); Si Young Lee, Ansan-si (KR); Ji Hye Sung, Seoul (KR)

(73) Assignee: G-TREEBNT CO., LTD., Seongnam-si (KR)

(*) Notice: Subject to any disclaimer, the term of this patent is extended or adjusted under 35 U.S.C. 154(b) by 0 days.

(21) Appl. No.: 15/520,915

(22) PCT Filed: Aug. 18, 2015

(86) PCT No.: PCT/KR2015/008621
§ 371 (c)(1),
(2) Date: Apr. 21, 2017

(87) PCT Pub. No.: WO2016/064078
PCT Pub. Date: Apr. 28, 2016

(65) Prior Publication Data
US 2017/0333531 A1    Nov. 23, 2017

(30) Foreign Application Priority Data

Oct. 22, 2014 (KR) .................. 10-2014-0143585
Oct. 22, 2014 (KR) .................. 10-2014-0143606

(51) Int. Cl.
*A61K 38/22* (2006.01)
*A61K 9/00* (2006.01)
*A61K 38/04* (2006.01)
*A61K 38/16* (2006.01)
*A61K 38/17* (2006.01)
*A61K 47/02* (2006.01)
*A61K 9/08* (2006.01)
*A61K 47/12* (2006.01)

(52) U.S. Cl.
CPC ........ *A61K 38/2292* (2013.01); *A61K 9/0048* (2013.01); *A61K 9/08* (2013.01); *A61K 38/04* (2013.01); *A61K 38/16* (2013.01); *A61K 38/17* (2013.01); *A61K 47/02* (2013.01); *A61K 47/12* (2013.01)

(58) Field of Classification Search
CPC .............................. A61K 38/2292; A61K 9/08
See application file for complete search history.

(56) References Cited

U.S. PATENT DOCUMENTS

| | | |
|---|---|---|
| 2003/0060405 A1 | 3/2003 | Kleinman et al. |
| 2009/0118196 A1 | 5/2009 | Crockford et al. |
| 2010/0267751 A1 | 10/2010 | Beals et al. |
| 2011/0020449 A1 | 1/2011 | Goldstein et al. |
| 2012/0264681 A1 | 10/2012 | Braiman-Wiksman et al. |

FOREIGN PATENT DOCUMENTS

| | | |
|---|---|---|
| EP | 2 311 485 A1 | 4/2011 |
| KR | 10-2008-0033939 A | 4/2008 |
| KR | 10-1258316 B1 | 4/2013 |
| WO | 2008/108927 A2 | 9/2008 |

OTHER PUBLICATIONS

Sosne et al., The FASEB Journal, 2010, 24:2144-2151. (Year: 2010).*
Gabriel Sosne et al., "Thymosin beta 4:A novel corneal wound healing and anti-inflammatory agent", Clinical Ophthalmology, 2007, pp. 201-207, vol. 1, No. 3.
Gabriel Sosne et al., "Thymosin β4: a potential novel dry eye therapy", Annals of the New York Academy of Sciences, 2012, pp. 45-50, vol. 1270.
Internal Search Report for PCT/KR2015/008621, dated Nov. 16, 2015.

* cited by examiner

*Primary Examiner* — Kaipeen E Yang
(74) *Attorney, Agent, or Firm* — Sughrue Mion, PLLC (57) ABSTRACT

The present invention relates to a therapeutic agent for ophthalmic disease containing thymosin beta 4. The present invention is more effective in reducing xerophthalmia than an ophthalmic solution containing cyclosporine A, is less irritant to eyes than conventional ophthalmic solutions and is physiochemically safe.

7 Claims, 3 Drawing Sheets

Specification includes a Sequence Listing.

COMPOSITION CONTAINING THYMOSIN BETA 4, AND PHARMACEUTICAL FORMULATION COMPRISING SAME

CROSS REFERENCE TO RELATED APPLICATIONS

This is a National Stage of International Application No. PCT/KR2015/008621 filed Aug. 18, 2015, claiming priority based on Korean Patent Application No. 10-2014-0143585 filed Oct. 22, 2014 and Korean Patent Application No. 10-2014-0143606 filed Oct. 22, 2014, the contents of all of which are incorporated herein by reference in their entirety.

TECHNICAL FIELD

The present invention pertains to a therapeutic agent for ophthalmic diseases, including thymosin beta 4.

BACKGROUND ART

Tears may include normal tears and reflex tears. Normal tears are secreted continuously, whilst reflex tears are secreted temporarily in a reflex response to stimuli such as pain, dust, spicy taste, smoke, odor, emotions of joy or sadness, or lack of tears. The tears secreted exist on the surface of the cornea to cover the surface of the eye and may play a role in protecting the eye and making it smooth, smoothing the surface of the cornea to secure a field of optical vision, preventing injury on epithelial cells of the cornea and conjunctiva, providing antibacterial activity against external bacteria, and supplying nutrition to the cornea. The tear is composed of a mucous layer, a water layer and a fat layer, and a volume of approximately 2 to 3 mL is generated per day to play the roles described above. However, if even at least one of these layers in the tear is lacking enough to cause a change in the tear film or a shortage in the volume of generated tears, the eye becomes dry and the tear cannot perform its function and this will ultimately cause dry eye syndrome.

Dry eye syndrome refers to an abnormal condition in terms of the amount and/or quality of tears independent of kerato-conjunctivitis disorder [Masakazu YAMADA et al., Nippon Ganka Kiyo, 43, 1289-1293 (1992)]. Furthermore, dry eye syndrome includes all diseases in association with an abnormal change in the tear film or a shortage in secretion of tears and also includes, for example, stimulus symptoms such as feelings of stimulus, discomfort and/or dryness caused by an injury on the surface of the eyeball due to a lack of tears, evaporation of tears or imbalance in the components of the tear, and corneitis, a wound on film epithelium, or the like. Dry eye syndrome may include dry conjunctiva syndrome, dry kerato-conjunctivitis, etc. as representative examples thereof, however, may not be particularly limited thereto.

In general, dry eye syndrome mostly occurs due to a shortage in the amount of tears or deterioration in function with ageing, and therefore is often discovered in women in middle age or aged persons. Other than the above, it was also reported that dry eye syndrome may be caused in association with inflammation, taking medicine (i.e., medicines for hypertension, hyperacid, neurosis, hypochondria, etc.), external wounds, chronic conjunctivitis, abnormal condition in eyelids, prostate gland disease and the like. In most cases, the exact cause is still unknown, but it was recently discovered that dry eye syndrome may occur due to autoimmune diseases caused by abnormal immune reactions.

An immune response is a reaction to protect the body from invasion of external (pathogenic) bacteria, and an autoimmune disease refers to a condition where the defense mechanism of the body, that is the immune system, has an abnormality and therefore attacks and destroys its own healthy cells and tissues due to a hypersensitive immune reaction. It is considered that autoimmune disease occurs due to an improper immune response induced by a change in cytokine (the signal substance for controlling and stimulating the defense system of the body against virus or bacteria) in the body, which in turn, excessively or improperly controls the autoimmune response. The exact etiology is not yet known, but the current discussion is that an autoimmune disease may arise from environmental factors, genetic factors and/or immunological factors.

At present, most autoimmune diseases are treated or prevented using steroids or immunosuppressive agents. Among these, a representative example of drugs for treating or preventing the dry eye syndrome of mammals including the human is RESTASIS™, available from Allergan PLC., which is 0.05% (w/v) cyclosporine A eye drop (U.S. Pat. No. 5,474,979).

The cyclosporine A is a non-soluble medicine with a water solubility of approximately 20 mg/ml to 30 mg/ml and RESTASIS™ is prepared in a micro-emulsion form including a liquid-liquid dispersion. However, the micro-emulsion is thermodynamically unstable, often causing improper conditions such as cohesion, sedimentation, creaming, growth of particles or adhesion, and has such a drawback that the liquid-liquid dispersion is easily broken. Therefore, in order to produce more stable particles, there was an attempt to reduce the size of the particle on the nano scale and prepare it in a nano-emulsion form (Korean Patent No. 1008189). However, a process for manufacturing the nano-emulsion needs expensive equipment such as a high-pressure homogenizer or micro-fluidizer, and may cause deterioration in the equipment, thus having a disadvantage of requiring much efforts and high production costs.

Furthermore, RESTASIS™ is a castor oil-based emulsion having a short storage time. Additionally, although RESTASIS™ is most broadly utilized as a medicine for the treatment or prevention of dry eye syndrome recently, the most suitable bioavailability thereof is not yet known. For instance, it may take several weeks to achieve the ideal effects of RESTASIS™. In this case, bioavailability means the percentage of a drug detected in a target eye tissue after administering the same. Herein, the detection of drug may be performed in aspects of pharmacodynamics (quantification of biological response to cyclosporine A) or pharmacokinetics (quantification of concentration of an actual medicine).

Therefore, in dry eye syndrome treatment or prevention applications, demands for formulations with more enhanced physical-chemical stability and drugs with more improved bioavailability have been continued, and in order to overcome these problems, studies on thymosin beta 4 are being conducted.

Thymosin beta 4 is a protein that was first discovered in the thymus gland in 1981, and it comprises 41 to 43 amino acids and has an isoelectric point of 5.1. In 1991, thymosin beta 4 was originally found as an actin-sequestering molecule from animal cells by Liva et al., and thereafter was disclosed to express immune-regulatory and neuro-endocrine effects.

Meanwhile, it was reported that thymosin beta 4 not only has the function of terminal deoxynucleotide transferase in thymocytes, but also increases movement of macrophages and antigens of the same and secretion of luteinizing hormone by hypothalamic explants. Furthermore, it is known that the above substance eliminates toxicity of cytosine arabinoside and inhibits a cell cycle of hematopoietic stem cells in order to increase adhesion and movement of endothelium. Moreover, Korean Patent Laid-Open Publication No. 10-2008-0033939 discloses the use of an ophthalmic solution (that is, eye drop solution) including a germicidal and active preservative as well as thymosin beta 4 for treating infection of eye, infectious disease (by bacteria, fungi or virus) and glaucoma.

However, the optimal combination and contents of individual components in an eye drop composition for treating dry eye syndrome are still not yet disclosed in any documents including the above Korean patent laid-open publication. Therefore, the present inventors have made efforts to improve disadvantages of conventional drugs and formulations proposed for the treatment and prevention of dry eye syndrome, and have found most suitable components including thymosin beta 4 and their proportions as well as most effective administration doses thereof.

DISCLOSURE

Technical Problem

An object of the present invention is to provide an optimal eye drop composition containing thymosin beta 4 and an optimal daily dosage thereof.

Technical Solution

In order to accomplish the object of the present invention, there is provided a pharmaceutical composition for the treatment or prevention of dry eye syndrome, which includes thymosin beta 4, sodium chloride, potassium chloride, calcium chloride dihydrate and magnesium chloride hexahydrate.

Advantageous Effects

The pharmaceutical composition of the present invention is more effective in improvement of dry eye syndrome than an eye drop containing cyclosporine A. Advantages of the present invention include and are not limited to reduced eye stimulation, enhanced physicochemical stability and a longer storage period as compared to conventional eye drops. Particularly, the present invention may achieve excellent stability while minimizing the use of any additive(s), compared to conventional eye drops.

BEST METHOD

In order to accomplish the objects of the present invention, the present invention provides a pharmaceutical composition for the treatment or prevention of dry eye syndrome, which includes thymosin beta 4, sodium chloride, potassium chloride, calcium chloride dihydrate and magnesium chloride hexahydrate.

The term "thymosin β4" as used herein refers to a polypeptide composed of 43 amino acids having 4.9 kDa, which is occasionally called thymosin beta-4 or Tβ4. This protein is upregulated during in vitro migration and differentiation of endothelial cells. A number of thymosin β4 isotypes have been discovered so far and have homology of approximately 70% or more, approximately 75% or more or approximately 80% or more with the known amino acid sequences of thymosin β4. Thymosin β4 in accordance with the present invention may also be an N-terminal mutant or a C-terminal mutant of wild type thymosin β4. Preferably, thymosin β4 in accordance with the present invention is the protein having an amino acid sequence denoted by SEQ ID No. 1. A concentration of thymosin beta 4 may range from 0.01 to 1.0% (w/v) preferably from 0.05 to 0.5% (w/v).

Furthermore, a concentration of sodium chloride may range from 0.1 to 1.2% (w/v) or from 0.3 to 1.0% (w/v). Preferably, it ranges from 0.5 to 0.7% (w/v). Furthermore, a concentration of potassium chloride may range from 0.01 to 0.15% (w/v) or from 0.03 to 0.12% (w/v). Preferably, it ranges from 0.05 to 0.09% (w/v). Furthermore, a concentration of calcium chloride dihydrate may range from 0.01 to 0.12% (w/v) or from 0.03 to 0.09% (w/v). Preferably, it ranges from 0.03 to 0.06% (w/v). Furthermore, a concentration of magnesium chloride hexahydrate may range from 0.01 to 0.12% (w/v) but preferably from 0.01 to 0.05% (w/v).

Meanwhile, the pharmaceutical composition in accordance with the present invention may further include hydrochloric acid or sodium hydroxide. Hydrochloric acid or sodium hydroxide may be suitably added to adjust a pH of the composition. The pH of the composition may be pH 6.5 to 7.5, or pH 6.8 to 7.2. Preferably, the composition may have pH 7.0.

Additionally, the pharmaceutical composition in accordance with the present invention may further include acetic acid or citric acid.

Acetic acid used herein is a weak acid represented by formula $CH_3COOH$. In the present invention, this may also be used in the form of acetate. One embodiment of the acetate may be sodium acetate trihydrate. Acetic acid or its salt may be included in an amount of 0.01% (w/v) to 1.5% (w/v) based on the total volume of the composition. Furthermore, acetic acid or its salt may be included in an amount of 0.1% (w/v) to 0.8% (w/v) but preferably 0.2% (w/v) to 0.5% (w/v).

Citric acid used herein is a compound represented by formula $C_6H_8O_7$. In the present invention, this may also be used in the form of citrate. The citrate is a derivative of citric acid, and embodiments of the citrate may be sodium citrate and sodium citrate dihydrate. Citric acid and its salt are generally used as buffers to limit the change in pH; the present invention needs quite a larger amount of citric acid or its salt than that commonly used in the art. In this case, citric acid or its salt may be included in an amount of 0.01% (w/v) to 0.5% (w/v). Furthermore, citric acid or its salt may be included in an amount of 0.05% (w/v) to 0.25% (w/v) preferably 0.1% (w/v) to 0.3% (w/v).

The composition in accordance with the present invention may be prepared as a formulation available for ophthalmic application. More specifically, the formulation may include, for example, solution, lotion, plaster, gel, cream, paste, spray, suspension, dispersion, hydrogel, ointment, oil, foaming agent, etc.

The composition may include 0.01% (w/v) to 1.5% (w/v) preferably 0.05% (w/v) to 0.5% (w/v) of thymosin beta 4.

Furthermore, the composition may be formulated into a unit-dosage form to provide a total daily dosage of 0.08 to 2.0 ml, and for that purpose it may be suitably dispensed into a container for ophthalmic use, which may facilitate quantitative administration of the composition. For this purpose, the composition may be formulated into a unit-dosage form with a dosage of 0.01 to 10 ml that can be used once or several times. Furthermore, in order to suitably provide the pharmaceutical composition in a total daily dosage of 0.08 to 2.0 ml, the composition may be contained in an eye drop container dropping 0.01 to 2.0 ml per droplet.

According to another aspect of the present invention, there is provided a method for the treatment of dry eye syndrome, which involves administration of the above composition to the subject.

More particularly, the present invention provides a treatment method, which comprises contacting an eye tissue with an effective amount of a composition including thymosin β4 as an active ingredient. An example of direct administration may include directly applying the composition in the form of, for example, a solution, lotion, plaster, gel, cream, paste, spray, suspension, dispersion, hydrogel, ointment, oil or foaming agent to the subject in order to ensure contact with eye tissues.

Furthermore, the composition may be formulated into a unit-dosage form to provide a total daily dosage of 0.08 to 2.0 ml, and for that purpose it may be suitably dispensed into a container for ophthalmic use, which may facilitate quantitative administration of the composition. For this purpose, the composition may be formulated into a unit-dosage form that can be used once or several times with a dosage of 0.01 to 10 ml. Furthermore, in order to suitably provide the pharmaceutical composition in a total daily dosage of 0.08 to 2.0 ml, the composition may be contained in an eye drop container dropping 0.01 to 2.0 ml per droplet. Preferably, the composition may be administered in the amount described above b.i.d. to q.i.d.

According to another aspect of the present invention, there is provided an eye drop containing thymosin β4 prepared in the manner described above. Thymosin β4 formulated as described above is not exposed to oxygen or heat, and can therefore be stable and retain its activity for a long period of time. Because the activity of thymosin β4 is retained for a long time, the eye drop in accordance with the present invention may maintain its pharmacological effects for a long period of time.

MODE FOR INVENTION

Hereinafter, in order to better understand the present invention, it will be described in more details by the following examples. However, such examples may include different variations or modifications, so it should not be construed that the scope of the present invention is limited within the scope of the following examples.

Process of Eye Drop Manufacture

The eye drop of the present invention may be manufactured according to the following process:

1-1. Weighing

The raw materials, reagents and a solvent are weighed, respectively.

1-2. Mixing

The weighed reagents are respectively placed in sterile water for injection as a solvent and mixed to be completely dissolved therein. Next, a weighed amount of thymosin beta 4 is added to the mixture and mixed until it is completely dissolved therein.

1-3. Adjustment of pH

After completing the mixing, the solution is adjusted to pH 7.0 by using sodium hydroxide and hydrochloric acid.

1-4. Filtering

Subsequent to adjustment, the solution is filtered through a 0.2 μm filter.

1-5. Filling

Subsequent to filtration, the mixture is dispensed into a low-density polyethylene container, followed by sealing the container.

[Drug]

For the sake of the desired effects of the present invention, thymosin beta 4 is preferably contained in a concentration of 0.05 to 0.5% (w/v) based on the total volume of the composition and, most preferably, in a concentration of 0.1% (w/v).

[pH Modifier]

The ophthalmic formulation may be manufactured to have a pH value similar to the physiological pH of tears in view of comfort, tolerance and stability in use.

The pH value of tears is approximately 7.4. However, when the eye is stimulated by its exudates or blinking, the pH of tears is reduced. Contrastingly, if the eyelids remain open for an extended time, a tear film is alkalized by equilibrium with a partial pressure of $CO_2$ in the surrounding air, and thus the pH of the tear becomes pH 9.0 or more.

The ophthalmic formulation manufactured herein may have pH 3.5 to 11.5, preferably, pH 3.5 to 9.0, more preferably, pH 4.5 to 8.0 and most preferably pH 5.5 to 7.8. For this purpose, the composition of the present invention may further include hydrochloric acid and/or sodium hydroxide.

[Other Excipients]

For the sake of the desired effects of the present invention, the composition may include 0.5 to 0.7% (w/v) of sodium chloride, 0.05 to 0.09% (w/v) of potassium chloride, 0.03 to 0.06% (w/v) of calcium chloride dihydrate and 0.01 to 0.05% (w/v) of magnesium chloride hexahydrate based on the total volume of the composition. Most preferably, the composition includes 0.6 to 0.7% (w/v) of sodium chloride, 0.07 to 0.08% (w/v) of potassium chloride, 0.04 to 0.05% (w/v) of calcium chloride dihydrate, and 0.02 to 0.04% (w/v) of magnesium chloride hexahydrate based on the total volume of the composition.

According to one embodiment, the composition of the present invention may further include 0.2 to 0.5% (w/v) of sodium acetate trihydrate and/or 0.1 to 0.3% (w/v) of sodium citrate dihydrate based on the total volume of the composition to produce more excellent effects of the present invention.

[Dosage and Administration]

The composition of the present invention including 0.05 to 0.5% (w/v) of thymosin beta 4 may exhibit optimal effects while minimizing stimulation on the eyes and other side effects when it contacts with the eye tissues in a total daily dosage of 0.08 to 2 ml once or several times a day. For this purpose, the composition of the present invention may be formulated in a unit-dosage form with a volume of 0.01 to 10 ml for use once or several times a day. Furthermore, such a unit-dosage form may be contained in an eye drop container dropping 0.01 to 2.0 ml per droplet, so as to suitably provide the above-described total daily dosage.

Examples 1 Through 5: Preparation of the Eye Drops

The eye drops were prepared with the compositional ratios shown in Table 1 below. Unless otherwise indicated, numerical values in Table 1 refer to a concentration of % (w/v) based on the total volume of the composition. For instance, the concentration of thymosin beta 4 in Example 1 is 0.05% (w/v), the concentration of thymosin beta 4 in Example 2 is 0.1% (w/v), the concentration of thymosin beta 4 in Example 3 is 0.5% (w/v), the concentration of thymosin beta 4 in Example 4 is 1% (w/v) and the concentration of thymosin beta 4 in Example 5 is 2% (w/v).

TABLE 1

| Component | Example 1 | Example 2 | Example 3 | Example 4 | Example 5 |
| --- | --- | --- | --- | --- | --- |
| Thymosin beta 4 | 0.05 | 0.1 | 0.5 | 1 | 2 |
| Sodium chloride | 0.64 | 0.64 | 0.64 | 0.64 | 0.64 |
| Potassium chloride | 0.075 | 0.075 | 0.075 | 0.075 | 0.075 |
| Calcium chloride dihydrate | 0.048 | 0.048 | 0.048 | 0.048 | 0.048 |
| Magnesium chloride hexahydrate | 0.03 | 0.03 | 0.03 | 0.03 | 0.03 |
| Sodium acetate trihydrate | 0.39 | 0.39 | 0.39 | 0.39 | 0.39 |
| Sodium citrate dihydrate | 0.17 | 0.17 | 0.17 | 0.17 | 0.17 |
| Hydrochloric acid | Added if required for adjustment to pH 7.0 | Added if required for adjustment to pH 7.0 | Added if required for adjustment to pH 7.0 | Added if required for adjustment to pH 7.0 | Added if required for adjustment to pH 7.0 |
| Sodium hydroxide | Added if required for adjustment to pH 7.0 | Added if required for adjustment to pH 7.0 | Added if required for adjustment to pH 7.0 | Added if required for adjustment to pH 7.0 | Added if required for adjustment to pH 7.0 |
| Sterile water for injection | Amount enough to make 100% (w/v) | Amount enough to make 100% (w/v) | Amount enough to make 100% (w/v) | Amount enough to make 100% (w/v) | Amount enough to make 100% (w/v) |

Meanwhile, Comparative Example 1 was RESTASIS™ comprising 0.05% (w/v) of commercially available cyclosporine.

Experimental Example 1: Storage Stability Test

In order to investigate stability after storage of the products of Example 2 and Comparative Example 1, both eye drops were stored at room temperature (15 to 25° C.) and under refrigeration for 70 days. Then, the appearance of the compositions was observed and titers of the drug in the compositions were determined by HPLC. Immediately after the preparation, the content of thymosin beta 4 in Example 2 was 1 mg/ml, whilst the content of cyclosporine in Comparative Example 1 was 0.5 mg/ml. HPLC was performed under the following conditions:

Column: Waters Delta-Pak C185 μm (3.9×150 mm)

Mobile phase A: Water containing 0.1% TFA. B: acetonitrile containing 0.1% TFA

Flow rate: 1.0 mL/min

Detection: UV 205 nm

Column temperature: Room temperature

Input volume: 10 mL

TABLE 2

| | Gradient | |
| --- | --- | --- |
| Time (min) | % A | % B |
| 0.0 | 85% | 15% |
| 15.0 | 75% | 25% |
| 15.1 | 20% | 80% |
| 17.0 | 20% | 80% |
| 17.1 | 85% | 15% |
| 26.0 | 85% | 15% |

The results are shown in Table 3:

TABLE 3

| | Example 2 | | Comparative Example 1 | |
| --- | --- | --- | --- | --- |
| | Appearance | Titer of drug | Appearance | Titer of drug |
| Immediately after preparation | Clear, transparent solution | 1 mg/ml | White, opaque or slightly translucent, and homogeneous liquid | 0.5 mg/ml |
| 70 days after storage at room temperature | Clear, transparent solution | 0.993 mg/ml | Precipitate occurred | Not measurable |

TABLE 3-continued

| | Example 2 | | Comparative Example 1 | |
|---|---|---|---|---|
| | Appearance | Titer of drug | Appearance | Titer of drug |
| 70 days after storage in refrigerator | Clear, transparent solution | 0.998 mg/ml | Precipitate occurred | Not measurable |

As such, the composition of Example 2 exhibits more excellent storage stability compared with that of Comparative Example 1.

Experimental Example 2: Verification of Improvement in Dry Eye Symptom

Experiments were performed in the mouse model with dry eye syndrome to determine effects of treating dry eye syndrome by the compositions of Examples 2, 4 and 5 containing different concentrations of thymosin beta 4, compared with a placebo control (formulation without thymosin beta 4). In order to induce the dry eye symptoms, female mice aged 8 weeks C57BL/6 were used, and eight mice per each group were subjected to the experiment under controlled adverse environment (CAE). In order to inhibit the generation of tears and aggravate dry eye disease symptoms, 0.5 mg/0.2 ml of scopolamine hydrobromide was injected q.i.d. between Day 6 and Day 10 after administering the test drug. The test drug was administered in a total daily dosage of 0.005 ml four times a day for 14 days and, in order to determine the treatment effects, a corneal surface fluorescein staining test was carried out on days 9, 12 and 14, after administration of the test drug to observe a change in corneal surface fluorescein staining scores. For reference, the corneal surface fluorescein staining score is a method of quantifying the symptoms of dry eye syndrome, and a decrease in the score means an improvement in the symptoms.

Figure 1:
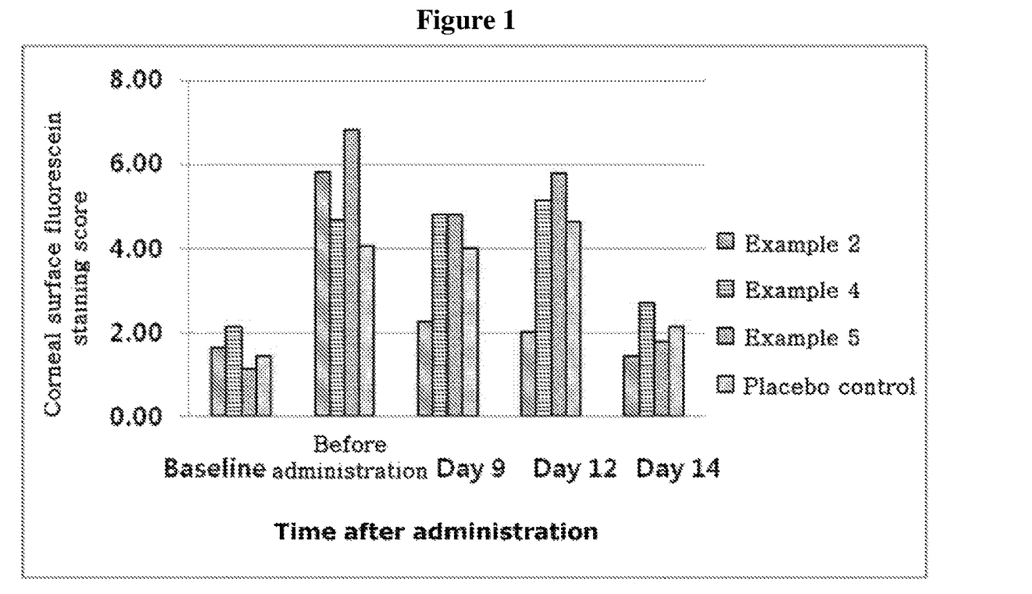
FIG. 1 illustrates changes in corneal surface fluorescein staining scores in relation to the time after administration of the respective products of the respective Examples 2, 4 and 5 and placebo control.
Figure 2:
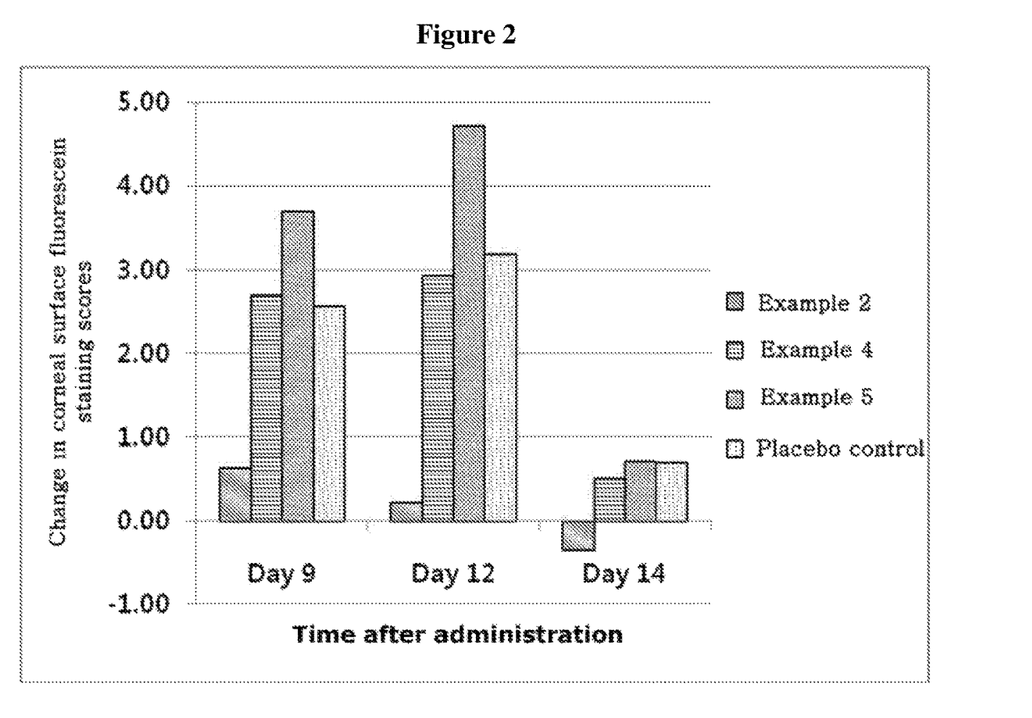
FIG. 2 illustrates changes from the baseline in corneal surface fluorescein staining scores in relation to the time after administration of the respective products of Examples 2, 4 and 5 and placebo control.
Figure 3:
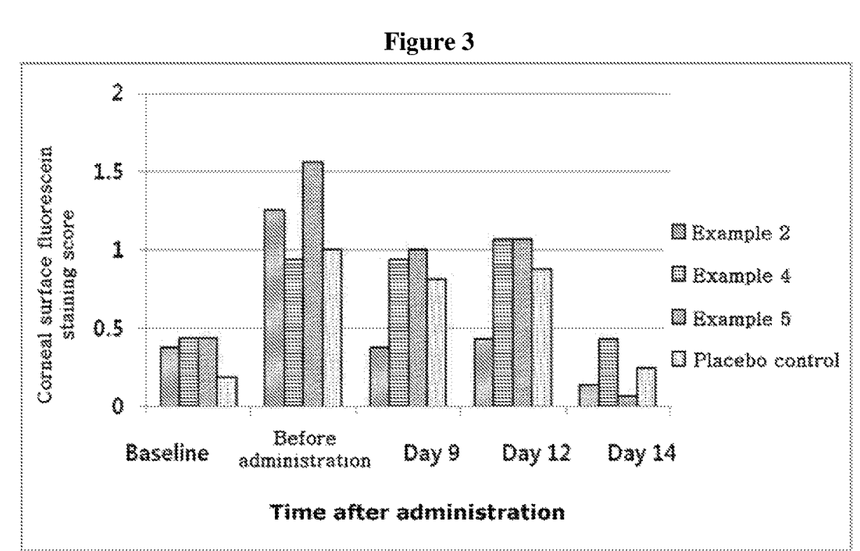
FIG. 3 illustrates changes from the baseline in fluorescein staining scores in relation to the time after administration of the respective products of Examples 2, 4 and 5 and placebo control.

Results of the experiments are shown in FIGS. 1, 2 and 3.

Referring to FIGS. 1 and 2, the baseline refers to a corneal surface fluorescein staining score in a healthy mouse before inducing dry eye syndrome. On the other hand, 'before administration' refers to a corneal surface fluorescein staining score in the mouse after inducing dry eye syndrome but before administering the test drug.

From the results shown in FIG. 1, the placebo control, Example 4 and Example 5 had an increase in the corneal surface fluorescein staining scores, whilst showing low corneal surface fluorescein staining scores at Day 14. No improvement effects were observed in these groups, compared to the baseline. However, Example 2 surprisingly had a significant effect in improving dry eye symptoms. Accordingly, it was found that the effect of thymosin beta 4 is not proportionate to the dosage administered.

FIG. 2 shows changes from the baseline in corneal surface fluorescein staining scores in relation to the times after administration. According to the results shown in FIG. 2, only Example 2 has improved the dry eye syndrome.

FIG. 3 shows changes in corneal surface fluorescein staining scores determined only in the inferior region of the cornea. According to the results shown in FIG. 3, although Examples 2 and 5 improved the dry eye syndrome as compared to the placebo control, only Example 2 produced such improvement without aggravating the symptoms.

Consequently, the composition of Example 2 was most effective in improvement of the dry eye syndrome.

Experimental Example 3: Determination of Desired Concentration for Improvement of Dry Eye Symptoms Effects of treating and improving the dry eye syndrome by administering the products of Examples 1 to 3 twice a day was tested in the dry eye syndrome mouse model. In order to induce symptoms of the dry eye syndrome, female mice aged 8 weeks C57BL/6 were used, and five mice per each group were subjected to the experiment under controlled adverse environment (CAE). In order to inhibit the generation of tears and aggravate symptoms of the dry eye, 0.5 mg/0.2 ml of scopolamine hydrobromide was injected q.i.d. between Day 6 and Day 10 after administering the test drug. Each test drug (Examples 1, 2 and 3) was administered in a total daily dosage of 0.005 ml twice a day for 6 days. In order to determine treatment effects, a corneal surface fluorescein staining test was carried out before administration and at Day 6 and Day 13 after administration, respectively, to observe a change in corneal surface fluorescein staining scores.

Figure 4:
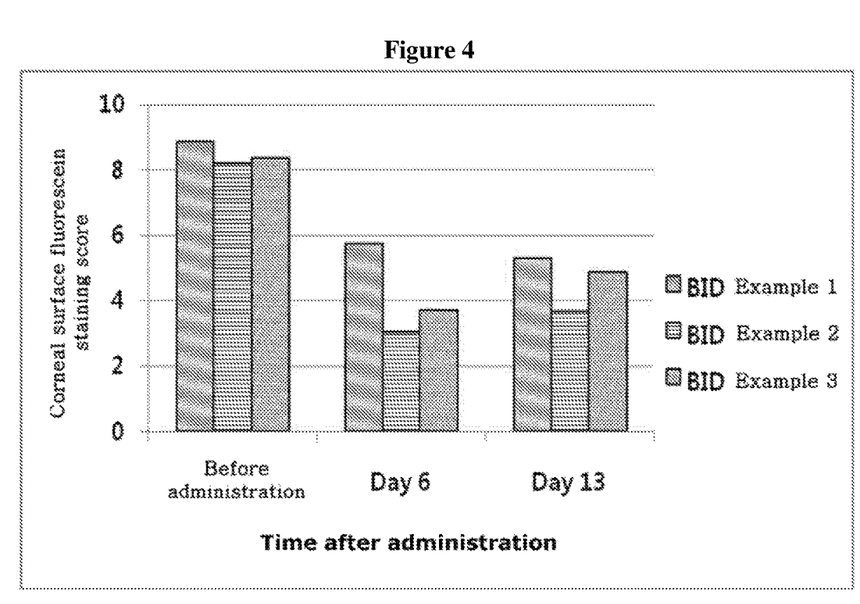
FIG. 4 illustrates changes in corneal surface fluorescein staining scores at Day 6 and Day 13 after administration of the respective products of Examples 1 to 3.

Results of the experiments are shown in FIG. 4.

From the results shown in FIG. 4, it can be seen that, as compared with the scores measured before administration, the experimental groups for b.i.d. administration of the products of Examples 2 and 3, exhibited a greater decrease in corneal surface fluorescein staining scores than the experimental group for b.i.d. administration of the product of Example 1. Particularly, the score of Example 2 was more decreased than that of Example 3.

Consequently, the drug concentration of Example 2 is more effective in improvement of dry eye syndrome, compared to those of Examples 1 and 3.

Experimental Example 4: Comparison with 0.05% (w/v) Cyclosporine (Comparative Example 1) in the Improvement of Dry Eye Symptoms In the dry eye syndrome mouse model, the effect of improving dry eye symptoms was compared between Example 2, Comparative Example 1 as an active control and a placebo control. In order to induce symptoms of the dry eye syndrome, female mice aged 8 weeks C57BL/6 were used, and five mice per each group were subjected to the experiment under controlled adverse environment (CAE). In order to inhibit the generation of tears and aggravate the dry eye disease symptoms, 0.5 mg/0.2 ml of scopolamine hydrobromide was injected q.i.d. between Day 6 and Day 10 after administering the drug. The test drug was administered in a total daily dosage of 0.005 ml twice a day for 6 days. In order to determine the treatment effects, a corneal surface fluorescein staining test was carried out before administration and at Day 6 and Day 13 after administration the test drug, respectively, to observe a change in corneal surface fluorescein staining scores.

Figure 5:
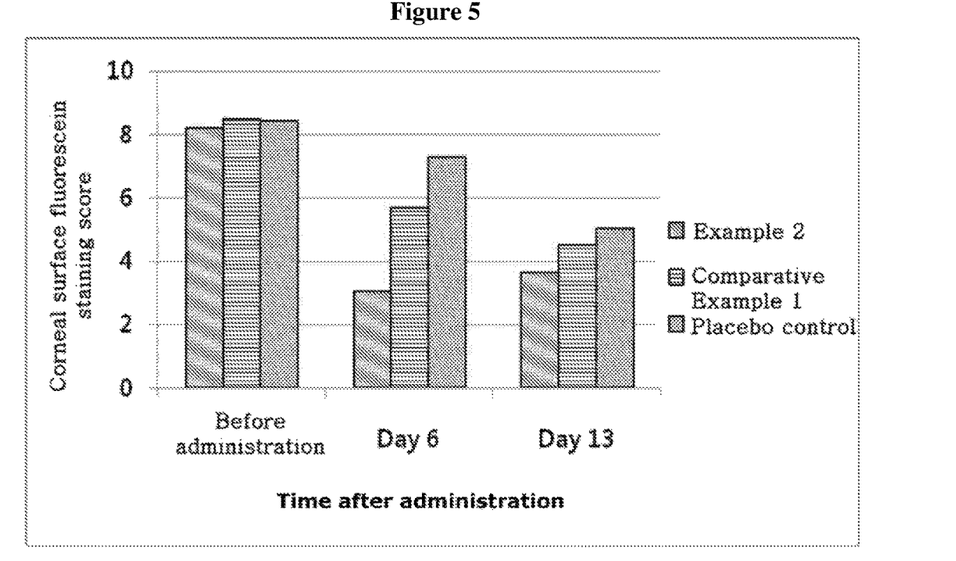
FIG. 5 illustrates changes in corneal surface fluorescein staining scores at Day 6 and Day 13 after administration of the respective products of Example 2, Comparative Example 1 and placebo control.

Results of the experiments are shown in FIG. 5.

From the results shown in FIG. 5, it can be seen that, as compared with the scores measured before administration, Example 2 exhibited a remarkably greater decrease in the corneal surface fluorescein staining score than Comparative Example 1 as the active control. More particularly, the administration of the product of Example 2 significantly decreased the corneal surface fluorescein staining till Day 5. Meanwhile from Day 6, scopolamine was administered in order to observe the effect of the test drug on the aggravation of the dry eye syndrome. As a result, it was found that administration of Example 2 remarkably inhibited the aggravation of the dry eye syndrome caused by scopolamine.

Experimental Example 5: Clinical Trial (Phase II)

Based on the non-clinical results described above, phase II clinical trial was conducted in order to compare safety and effectiveness between Example 2 and the placebo control, regarding the signs and symptoms of dry eye syndrome. This clinical trial was conducted under controlled adverse environment (CAE), in a single institute in both double-blind and random assignments, in order to compare 0.1% (w/v) thymosin beta 4 eye drop with the placebo control, regarding the test drug's safety and effectiveness. More specifically, 36 persons in each group were subjected to administration of the placebo control and the product of Example 2, respectively. A squeeze bottle for dropping 40 µl per droplet was used to administer 1 or 2 drops twice a day for 30 days. In order to determine the treatment effects, a corneal surface fluorescein staining test was carried out before administration and at Day 30 after administration, respectively, to observe a change in corneal surface fluorescein staining scores.

Figure 6:
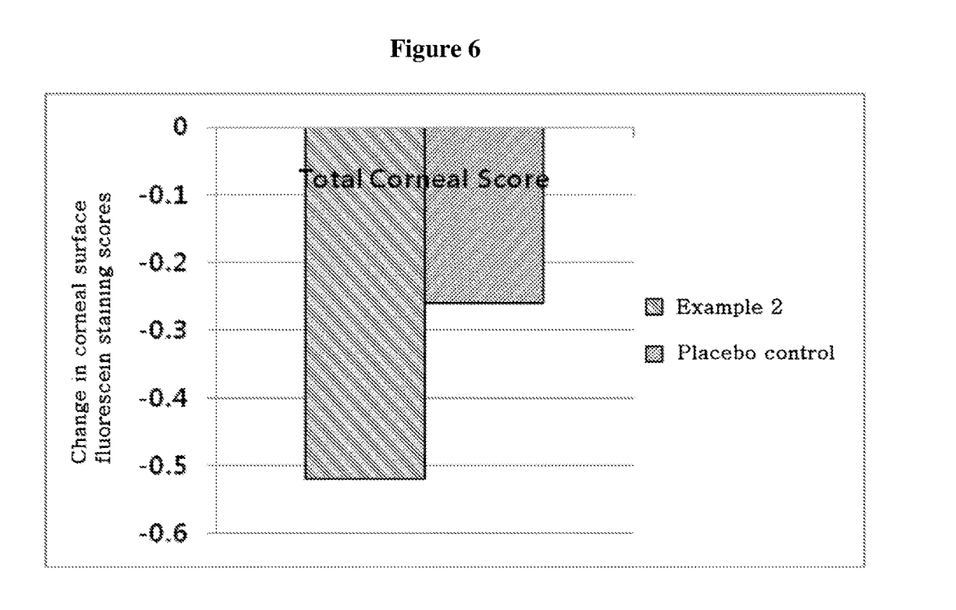
FIG. 6 illustrates changes in corneal surface fluorescein staining scores at Day 30 after administration of the respective products of Example 2 and placebo control.

Results of the experiments are shown in FIG. 6.

From the results shown in FIG. 6, a marked difference in corneal surface fluorescein staining was found after administering the product of Example 2 twice a day, as compared with the placebo control. Thus, in agreement with the non-clinical results, the results of this clinical trial confirm that Example 2 is effective in treatment of dry eye syndrome.

Experimental Example 6: Stimulation Test

The extent of the irritation caused by the eye drop was compared between Example 2 and Comparative Example 1.

Test scales: After administering an eye drop, the extent of discomfort, such as tingling in the eye or blurred vision, was measured with reference to a scale of 1 to 5, as follows: 1—very unsatisfied; 2—unsatisfied; 3—moderate; 4—satisfied; and 5—very satisfied.

The results were measured, as shown in Table 4 below.

TABLE 4

|  | Example 2 | Comparative Example 1 |
|---|---|---|
| Extent of irritation | 4.5 | 2.5 |

Consequently, Example 2 allowed users to feel more comfortable with less irritation, as compared to Comparative Example 1.

Sequence Listing Free Text

SEQ ID No. 1.:
SDKPDMAEIE KFDKSKLKKT ETQEKNPLPS KETIEQEKQA GES

The invention claimed is:

1. A method for preventing or treating dry eye syndrome in a mammal in need thereof, comprising administering to the mammal a composition comprising:
   (a) thymosin beta 4 in a concentration of from 0.05 to 0.5% (w/v);
   (b) sodium chloride in a concentration ranging from 0.5 to 0.7% (w/v);
   (c) potassium chloride in a concentration ranging from 0.05 to 0.09% (w/v);
   (d) calcium chloride dihydrate in a concentration of from 0.03 to 0.06% (w/v);
   (e) magnesium chloride hexahydrate in a concentration of from 0.01 to 0.05% (w/v);
   (f) sodium acetate trihydrate in a concentration ranging from 0.2 to 0.5% % (w/v); and
   (g) sodium citrate dihydrate in a concentration ranging from 0.1 to 0.3% (w/v),
   wherein the composition is administered at a total daily dosage of 0.08 to 2.0 ml;
   wherein the composition is in a unit dosage form to provide the total daily dosage of 0.08 to 2.0 ml; and
   wherein the composition is administered by droplet.

2. The method according to claim 1, wherein the composition further comprises hydrochloric acid or sodium hydroxide.

3. The method according to claim 1, wherein each droplet ranges from 0.01 ml to 0.04 ml.

4. The method according to claim 1, wherein the composition is in a unit dosage form which has a total volume ranging from 0.01 to 10 ml.

5. The method according to claim 4, wherein the unit dosage form is an eye drop container.

6. The method according to claim 1, wherein the composition is a clear and transparent solution.

7. The method according to claim 1, wherein the composition comprises
   (a) thymosin beta 4 in a concentration of about 0.1% (w/v);
   (b) sodium chloride in a concentration of about 0.64% (w/v);
   (c) potassium chloride in a concentration of about 0.075% (w/v);
   (d) calcium chloride dihydrate in a concentration of about 0.048% (w/v);

SEQUENCE LISTING

<160> NUMBER OF SEQ ID NOS: 1

<210> SEQ ID NO 1
<211> LENGTH: 43
<212> TYPE: PRT
<213> ORGANISM: Homo sapiens
<220> FEATURE:
<223> OTHER INFORMATION: thymosine beta 4

<400> SEQUENCE: 1

Ser Asp Lys Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
                20                  25                  30

Thr Ile Glu Gln Glu Lys Gln Ala Gly Glu Ser
                35                  40

(e) magnesium chloride hexahydrate in a concentration of about 0.03% (w/v);
(f) sodium acetate trihydrate in a concentration of about 0.39% (w/v); and
(g) sodium citrate dihydrate in a concentration of about 0.17% (w/v).

* * * * *